United States Patent
Giffey

(10) Patent No.: US 9,271,805 B2
(45) Date of Patent: Mar. 1, 2016

(54) ISOMARK NEEDLE

(75) Inventor: Broc T. Giffey, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 83 days.

(21) Appl. No.: 13/148,132

(22) PCT Filed: Feb. 4, 2010

(86) PCT No.: PCT/US2010/023133
§ 371 (c)(1),
(2), (4) Date: Oct. 4, 2011

(87) PCT Pub. No.: WO2010/091137
PCT Pub. Date: Aug. 12, 2010

(65) Prior Publication Data
US 2012/0029548 A1   Feb. 2, 2012

Related U.S. Application Data

(60) Provisional application No. 61/150,614, filed on Feb. 6, 2009.

(51) Int. Cl.
*A61B 17/34* (2006.01)
*A61B 19/00* (2006.01)
*A61B 5/11* (2006.01)
*A61N 5/10* (2006.01)

(52) U.S. Cl.
CPC .............. *A61B 19/54* (2013.01); *A61B 5/1127* (2013.01); *A61B 2019/545* (2013.01); *A61N 5/1049* (2013.01)

(58) Field of Classification Search
USPC .......................... 606/116, 181, 182, 185, 186
See application file for complete search history.

(56) References Cited

U.S. PATENT DOCUMENTS

| | | | |
|---|---|---|---|
| 1,489,558 A | | 4/1924 | Timson |
| 1,699,012 A | * | 1/1929 | Naylor ............................ 101/26 |
| 3,039,467 A | | 6/1962 | Stone et al. |
| 4,279,259 A | | 7/1981 | Lee et al. |
| 4,392,493 A | | 7/1983 | Niemeijer |
| 4,437,361 A | | 3/1984 | Steckel et al. |
| 4,440,168 A | * | 4/1984 | Warren ......................... 606/102 |
| 4,508,106 A | | 4/1985 | Angres |

(Continued)

FOREIGN PATENT DOCUMENTS

WO    WO2010091137 A2    8/2010

OTHER PUBLICATIONS

Definition of Indicia, www.dictionary.com, accessed on Nov. 18, 2013, 1 page.*

(Continued)

*Primary Examiner* — Tuan V Nguyen
(74) *Attorney, Agent, or Firm* — Faegre Baker Daniels LLP

(57) ABSTRACT

A device for marking a treatment isocenter on a patient's body includes a base including alignment indicia; a marker disposed over the base and positioned relative to the indicia for marking the isocenter on the patient's body; and an actuator for actuating the marker and causing a mark indicating the isocenter to be made on the patient's body. The actuator can include a button and a spring coupled to the marker. Compressing the actuator causes the marker to travel through an ink well prior to piercing the patient's skin. The device is disposable as intended for a single use.

9 Claims, 4 Drawing Sheets

(56) References Cited

U.S. PATENT DOCUMENTS

| | | | |
|---|---|---|---|
| 4,608,045 A | 8/1986 | Fretwell | |
| 4,665,912 A | 5/1987 | Burton | |
| 4,914,988 A | 4/1990 | Chang | |
| 5,026,388 A | 6/1991 | Ingalz | |
| 5,231,993 A * | 8/1993 | Haber et al. | 600/583 |
| 5,306,271 A | 4/1994 | Zinreich et al. | |
| 5,368,030 A | 11/1994 | Zinreich et al. | |
| 5,407,440 A | 4/1995 | Zinreich et al. | |
| 5,469,847 A | 11/1995 | Zinreich et al. | |
| 5,496,304 A * | 3/1996 | Chasan | 606/1 |
| 5,569,237 A | 10/1996 | Beckenstein | |
| 5,643,306 A * | 7/1997 | Schraga | 606/182 |
| 5,680,872 A * | 10/1997 | Sesekura et al. | 600/577 |
| 5,690,107 A | 11/1997 | Hofmann | |
| 5,713,890 A | 2/1998 | Chasan | |
| 5,743,899 A * | 4/1998 | Zinreich | 606/1 |
| 5,833,649 A | 11/1998 | Atef | |
| 5,988,174 A | 11/1999 | Chasan | |
| 5,997,501 A | 12/1999 | Gross et al. | |
| 6,056,737 A * | 5/2000 | Rosen | 606/1 |
| 6,197,034 B1 | 3/2001 | Gvozdic et al. | |
| 6,540,756 B1 | 4/2003 | Vaughan | |
| 6,588,301 B1 | 7/2003 | Chanet et al. | |
| 6,612,262 B2 | 9/2003 | Julien et al. | |
| 6,901,885 B1 | 6/2005 | Kleinsasser | |
| 6,923,816 B1 | 8/2005 | Passmore | |
| 7,166,852 B2 | 1/2007 | Saracen et al. | |
| 7,494,493 B2 | 2/2009 | Matsuura | |
| 8,480,684 B2 * | 7/2013 | Bendre et al. | 606/116 |
| 2003/0187458 A1 | 10/2003 | Carlson, II | |
| 2003/0195523 A1 | 10/2003 | Futsz | |
| 2004/0267283 A1 * | 12/2004 | Mavor et al. | 606/116 |
| 2005/0245948 A1 * | 11/2005 | Khalaj | 606/166 |
| 2005/0277973 A1 | 12/2005 | Huang et al. | |
| 2006/0079910 A1 | 4/2006 | Tartaglia | |
| 2007/0203504 A1 | 8/2007 | Denny et al. | |
| 2008/0051730 A1 * | 2/2008 | Bikovsky | 604/240 |
| 2008/0208236 A1 | 8/2008 | Hobbs et al. | |
| 2008/0269687 A1 * | 10/2008 | Chong et al. | 604/180 |
| 2008/0287782 A1 | 11/2008 | Traboulsi et al. | |
| 2008/0287978 A1 | 11/2008 | Hickman, III | |
| 2010/0004532 A1 * | 1/2010 | Bendre et al. | 600/426 |
| 2010/0137710 A1 | 6/2010 | Zavislan et al. | |
| 2014/0107662 A1 | 4/2014 | Goolishian | |

OTHER PUBLICATIONS

International Search Report and Written Opinion issued in PCT/US2010/023313, mailed Sep. 14, 2010, 8 pages.

* cited by examiner

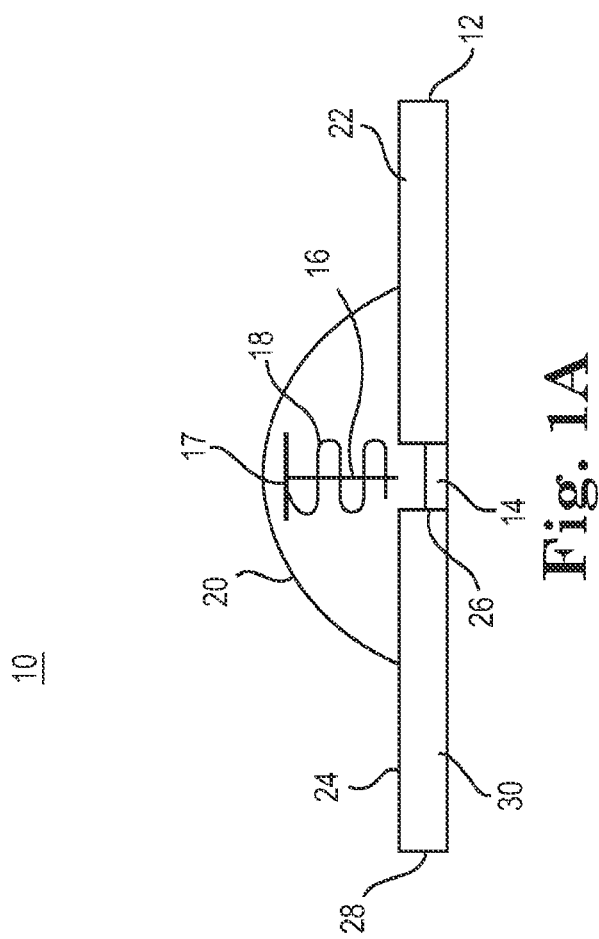

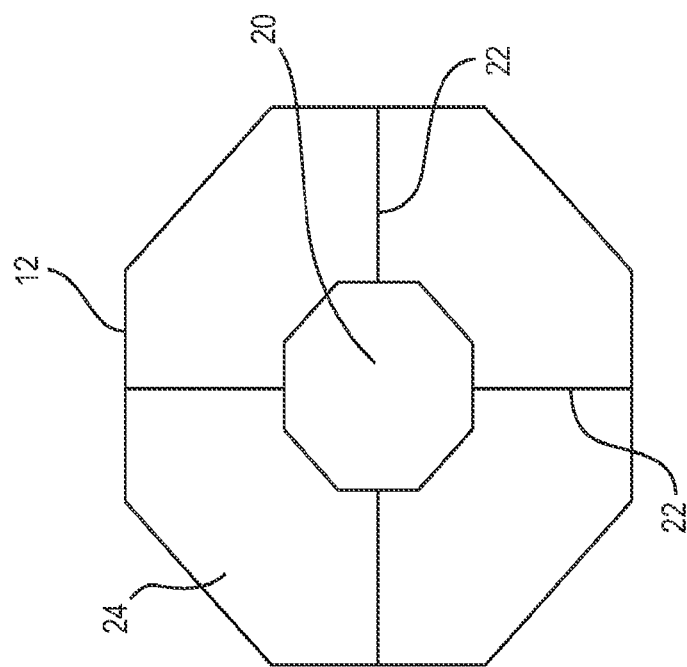

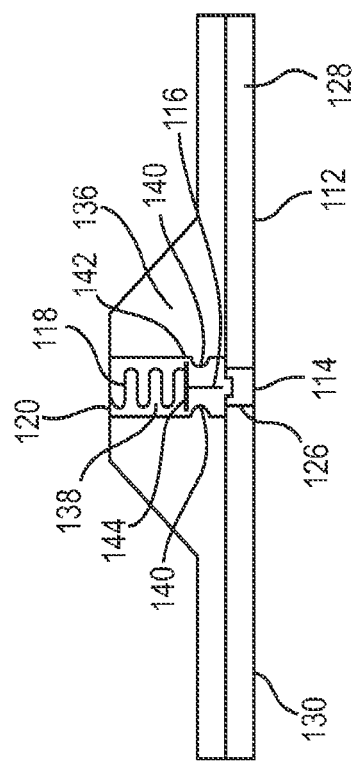

ISOMARK NEEDLE

CROSS REFERENCE TO RELATED APPLICATIONS

This application claims the benefit of U.S. provisional application No. 61/150,614, filed Feb. 6, 2009, entitled ISOMARK NEEDLE, the disclosure of which is hereby incorporated by reference in its entirety for all purposes.

TECHNICAL FIELD

The present invention relates to a marking device. More particularly, the present invention relates to a device and a method for marking a treatment isocenter on a patient's body.

BACKGROUND

Before receiving radiation therapy treatment, a computed axial tomography simulation (CAT scan or CT scan) must be performed. A CT scan is used to help the radiation oncologist map the target treatment area on a patient's body. Dosimetrists and physicists plan the entire treatment from the CT images. The CT scan is performed with the patient in a comfortable, yet stable position for the area being treated. With the patient in the desired treatment position, a CT scan is performed. Using the images from the scan, an oncologist determines a treatment isocenter. When the oncologist determines the isocenter, a computer generates the coordinates for a laser projecting system. The lasers project beams from the walls on both the right and left side of the patient as well as the ceiling, indicating the three points of the coordinates. The center at which the three points intersect in the body defines the isocenter.

External marks are then placed on the patient's skin and used to align the patient for treatment each day. These external marks will indicate where the isocenter or center of treatment is within the patient's body. When the patient is aligned to these marks, prior to treatment, the isocenter will fall directly under the central axis of the radiation beam. Lining a patient up to these marks ensures that they are in the same position for treatment as they were at the time of simulation. The marks are then tattooed. These tattoos will be used during the course of treatment to reproduce how the patient was positioned during the CT scan. If a patient is having head or neck treatment these external marks are usually placed on a mask using tape and a marker and no tattoo is needed.

The current technique for tattooing external marks on a patient's skin is performed immediately after the oncologist sets the isocenter. The lasers project from the walls and ceiling making an X on the right, left, and anterior or posterior side of the patient's body. A clinician uses a marker to trace where the lasers fall on the patient's skin. The X's that are drawn on the patient's skin are then tattooed for a permanent reference point. A drop of ink is then placed on the center of the X and with a 19 gauge needle the patient is stuck, creating a permanent tattoo. A piece of gauze is used to wipe off excess ink, and additional alcohol wipes are used to remove any remaining ink on the patient's skin. This procedure is repeated for each X that is drawn on the patient's body. The process can be very time consuming, and the patient must remain still until the entire process is completed.

There are disadvantages associated with the current technique described above. For example, it is very difficult to draw a straight line on a patient's body following a thin laser. When trying to follow the laser projected on the skin, the clinician's hand tends to block the laser, making it impossible to see where the line is being drawn. Second, the marker bleeds as the lines are drawn. Additionally, a line expected to be very precise becomes 3-5 mm thick. After drawing two lines with the sharpie, it is possible to be anywhere from 0.5 cm to 1 cm off the actual center of the X. One drop of ink is then placed in the center of the X. It becomes difficult determining where the tip of a 19 gauge needle should be placed on the smeared X which was drawn with a sharpie and now has a drop of ink on top of it.

There are also disadvantages associated with the use of ink droppers for tattoos. First, when only one drop of ink should be placed on the X, often times more than one drop comes out making it difficult or impossible to see the X. Second, some patients have very dry skin which soaks up the ink making it difficult once again to see the center of the X. Additionally, about 15-20 percent of patients need to be tattooed twice because the first tattoo is not visible. Treatment tolerances and deviations from these tattoos are within millimeters. On average, the margin of error planned for a treatment is only 2-5 mm. Unfortunately, a patient may already be marked up to 1.5 cm off their original coordinates defined by the oncologist.

Thus, there remains a need for improved devices and methods for marking isocenters on a patient's body.

SUMMARY

A device for marking a treatment isocenter on a patient's body includes a base including alignment indicia; a marker disposed over the base and positioned relative to the indicia for marking the isocenter on the patient's body; and an actuator for actuating the marker and causing a mark indicating the isocenter to be made on the patient's body.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 1A is a schematic, cross-sectional view of an isocenter marking device provided in accordance with an embodiment of the present invention.

FIG. 1B is a top-down, schematic view of the isocenter marking device shown in FIG. 1A.

FIG. 4 is a detailed schematic, cross-sectional view of an isocenter marking device provided in accordance with an embodiment of the present invention.

DETAILED DESCRIPTION

Figure 3A:
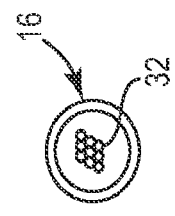
FIGS. 3A-3E are end views of the needle configurations shown in FIGS. 2A-2E.
Figure 3B:
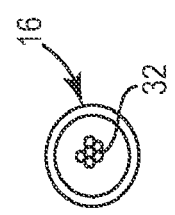
Figures 3C, 3D, 3E:
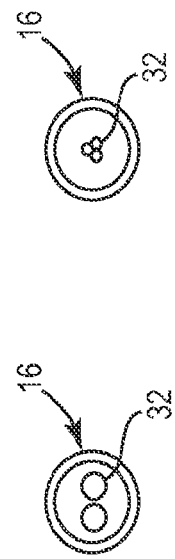

FIG. 1A is a schematic view of an isocenter marking device 10 according to an exemplary embodiment of the present invention. The isocenter marking device 10 can be used with any image modality including CT imaging. FIG. 1B is a schematic, top-down view of the device shown in FIG. 1A. As shown in FIGS. 1A and 1B, the isocenter marking device includes a base 12, an ink well 14, a marker 16, a spring 18, and a button 20. The device 10 can be provided in a sterile packaging. Additionally, the device 10 is disposable and is intended for a single use. After use, the device 10 should be disposed of in the appropriate waste receptacle.

In various embodiments, the base 12 includes alignment indicia 22 located on an upper surface 24 of the base 12, as best shown in FIG. 1B. The alignment indicia 22 facilitate alignment of the device 10, and in particular the marker 16, with laser beams that are projected onto a patient's skin during the mapping procedure. In one embodiment, the alignment indicia 22 can be raised surface features formed on the support surface 22 of the base 12. In another embodiment, the alignment indicia 22 can be depressed grooves formed in the upper surface 24 of the base 12. In some embodiments, the alignment indicia 22 include two or more orthogonal lines. Other forms of alignment indicia also can be incorporated onto or into the device 10. Additionally, in some embodiments, the base 12 can have a shape such that the points of the polygon can be aligned with the lasers that are projected onto the skin. The base 12 can have any number of shapes (irregular and polygonal) including but not limited to a triangular shape, a quadrangular shape, a pentagonal shape, a hexagonal shape, circular shape or octagonal shape (shown in FIG. 1B). In further embodiments, the base 12 can include one or more side tabs to facilitate ease of use.

According to various embodiments, and as shown in FIG. 1A, the base 12 also includes an ink reservoir or well 14. In some embodiments, the ink well 14 is defined by a spacer portion 26. The spacer portion 26 prevents the ink within the ink well 14 from leaking out of the device 10. Additionally, the spacer portion 26 supports the button 20 and the marker 16. In some embodiments, the spacer portion 26 limits the longitudinal movement of the marker 14 which may provide a consistent depth at which the patient's skin is pierced and may prevent the patient's skin being pierced at too deep a depth. In some embodiments, the spacer portion 26 allows the marker 16 to pierce the patient's skin at a depth ranging from about 2 mm to about 4 mm.

In some embodiments, the base 12 includes a conformal layer 28 fabricated from a material that facilitates conformation of the base 12 to the patient's skin. Exemplary materials for the conformal layer 28 include but are not limited to soft foam, rubber, plastic or other suitable materials. In certain embodiments, an overall thickness of the base 12 is about 0.5 cm.

In some embodiments, the base 12 also includes an adhesive layer 30 that is used to secure the device 10 to the patient's skin. The adhesive layer 30 can be covered by a peel-away label. The user removes the label prior to using the device. The label can include directions for use as well as safety information.

As shown in FIG. 1A, a marker 16 is disposed over the base 12. In various embodiments, the marker 16 is composed of one or more devices capable of piercing a patient's skin. In various embodiments, the marker 16 is composed of one or more of needles 32, as shown in FIGS. 2A-2E discussed below. In one embodiment, the needle(s) 32 can be hollow. In other embodiments, the needle(s) 32 can include a cavity 33 (shown in FIGS. 2A and 2B) in the tip region 34 of the needle. The cavity 33 is sized such that it is adapted to retain and deliver a metered dose of ink when the needle(s) 32 pierce a patient's skin. In still another embodiment, the needle(s) 32 can be solid.

Figure 2A:
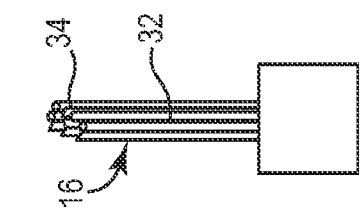
FIGS. 2A-2E are schematic views of various needle configurations for the marker in accordance with various embodiments of the present invention.
Figure 2B:
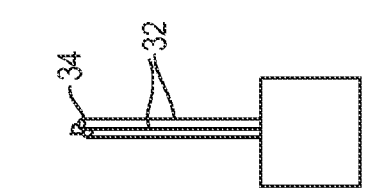
Figures 2C, 2D:
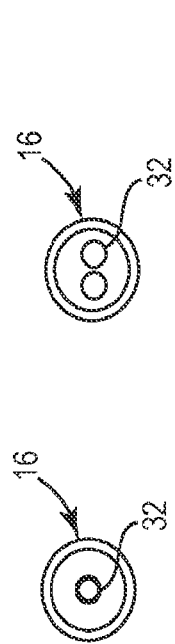
Figure 2E:
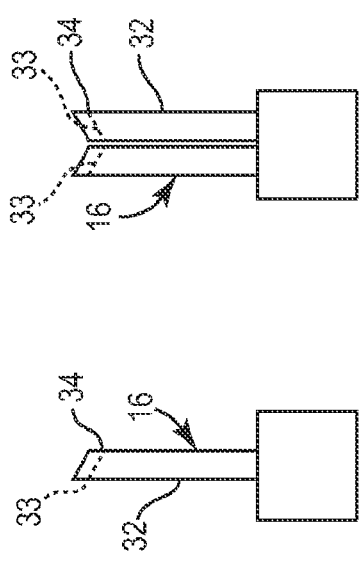

FIGS. 2A-2E show schematic views of various needle configurations suitable for use with the various embodiments of the present invention. FIGS. 3A-3E show end views of each of the needle configurations shown in FIGS. 2A-2E, respectively. The number, size, length and manner in which the individual needles 32 are arranged to form the marker 16 can vary. In some embodiments, the number of needles 32 can range from 1 to 9. In other embodiments, the number of needles 32 used to form the marker 16 can be 1, 2, 3, 6 or 9 needles. The needles 32 can also vary in gauge. For example, if a single needle 32 is used, such as shown in FIGS. 2A and 3A, a lower gauge (larger) needle can be selected. If multiple needles are used, such as shown in FIGS. 2C, 2D and 2E, a higher gauge (smaller) needle can be used. In one embodiment, the marker 16 can include a flat head 17 such that it has an overall T-shape cross-section.

As shown in FIG. 1A, the marker 16 is disposed over the base 12 such that it is positioned over the ink well 14. The marker 16 travels through the ink well 14 prior to piercing a patient's skin. The ink is picked up by the needle(s) 32 as they pass through the ink well 14 until the ink is pushed and/or released into the patient's skin. In one embodiment, the ink is retained in the hollow lumen or cavity of the needle(s) 32 until it is released into a patient's skin. In other embodiments (not shown), the ink is retained in or on the tip of the marker (e.g., as in writing instruments). Exemplary inks include, but are not limited to, the following: India ink, Carfusion dye, fluorescent inks, temporary inks, and permanent inks, among others. Additionally, the inks used can vary in color. For example, the color of the ink can be black, blue, white, silver, red, etc.

In various embodiments, the marker 16 is coupled to an actuator for actuating the marker 16 causing a mark indicating the isocenter to be made on the patient's body. In one embodiment, the actuator includes a spring 18 coupled to the marker 16. Compression of the spring 18 results in a downward movement of the marker 16, forcing the marker 16 through the ink well 14 and into the patient's skin resulting in a mark being made on the patient's body. In one embodiment, when compressive forces applied to the spring are released, the marker 16 is released and is retracted back through the base 10 such that the marker 16 is no longer exposed. In some embodiments, the actuator makes an audible sound when actuated.

In some embodiments, the actuator also includes a button 20 or other device coupled to the spring 18. Using their finger or thumb, the user applies a compressive force to the button 20 which in turn compresses the spring 18. According to some embodiments, when the button 20 is released, the compressive forces applied to the button are also released, resulting in retraction of the marker 16 into the device 10 such that the marker 16 is no longer exposed. Retraction of the marker 16 into the device 10 such that it is no longer exposed may prevent an accidental needle stick and may make the device safer for disposal. In some embodiments the base 12 is self-sealing and seals after the marker 16 has been retracted into the base 12. In some embodiments, the marker 16 can be inactivated from further by use by a safety mechanism provided in the device 10. For example, the spring 18 can be configured such that when rotated, further actuation of the spring 18 is prevented. Any known mechanism suitable for preventing re-actuation of the marker 16 can be employed. After the isocenter mark has been made at the desired location on the patient's body, the device 10 can be discarded in the appropriate waste receptacle.

FIG. 4 is a detailed, schematic view of an isocenter marking device 100 provided in accordance with other embodiments of the present invention. As shown in FIG. 4, the device 100 includes a marker 116 coupled to a spring 118 and a button 120 for actuating the marker 116. The marker 116 can be composed of one or more needles as described in detail above according to the various embodiments. The marker 116 is disposed over the base 112 such that it is centered over a spacer portion 126 defining an ink well 114. The base 112 includes a conformal layer 128 fabricated from a material that facilitates conformation of the base 112 to the patient's skin. Additionally, the base 112 includes an adhesive layer 130 for securing the base 112 to the patient's skin. The base 112 can have any one of the polygonal shapes as described above and includes alignment indicia on the base 112, as described above. The alignment indicia facilitate alignment of the device 100, and in particular the marker 116, with laser beams that are projected onto a patient's skin during the mapping procedure.

In some embodiments, as shown in FIG. 4, the device 100 includes a housing 136 positioned over the base 112. The marker 116, spring 118, and button 120 are centered within the housing 136. The housing includes a bore 138 for containing the spring 118 and the marker 116. In certain embodiments, the button 120 is sized such that when depressed, it is received within the bore 138. The housing 136 can be fabricated from an elastic material such as rubber or plastic and, in some embodiments, may flex upon a compressive force being applied to the button 120.

The device 100 also includes at least one pair of tabs 140 formed within the base 112. When no force is applied to the button 120 and the spring 118, the flat head 144 of the marker 116 rests on an upper surface 142 of the tabs 140. In one embodiment, when a compressive force is applied to the button 120 and the spring 118, forcing the marker 116 downward and through the inkwell, the tabs 140 will begin to move in a lateral direction away from the marker 116 facilitating the marker 116 to move past the tabs. In other embodiments, the tabs 140 remain fixed. When enough pressure is applied to the button 120, the flat head 144 of the marker 116 is pushed past the tabs 140.

The marker 116 travels downward through the ink well 114 and into the patient's skin. The length of travel of the marker 116 is limited by the conformal layer 128 and the spacer portion 126, thereby controlling the depth at which the patient's skin is pierced. Releasing pressure applied to the button 120 will permit the spring 118 to expand, retracting the marker 116 back into the base 112. The tabs 140 prevent the marker 140 from being fully retracted back to its starting position thereby limiting the device 100 to a single use.

It will be generally understood by those of skill in the art that the springs 18, 118 shown here in FIGS. 1A and 4 are exemplary in nature and that other spring configurations and biasing structures can be utilized. For example, a spring can be provided alongside and parallel to the marker 16, 116 facilitating a more compact configuration of the overall device.

Next, a method of using an isocenter marking device according to the various embodiments will be described. First, the adhesive layer on the device base is exposed. The alignment indicia are then aligned or matched with the laser beams projected on the patient and the device is then secured to the patient's skin. The alignment of the laser beams with the alignment indicia should be confirmed. The isocenter can then be marked by compressing the button on the device to actuate the spring-loaded marker located inside. The marker passes through the ink well and into the patient's skin. The end result is a permanent tattoo. Any excess ink present on the patient's skin is wiped away with an alcohol swab or wipe. The device is then discarded in the appropriate waste receptacle. These steps are repeated for each isocenter needing to be marked on the patient's body.

There are several advantages of using the isocenter marking device, as described above according to the various embodiments. One such advantage is efficiency. There is no time used to draw the X's using a marker or to place a drop of ink on the patient skin. These two steps take more time than aligning the isocenter marking device of the present invention with the laser beams and pressing the button to give the tattoo.

Additionally, the accuracy of the isocenter marking device may be superior as there is greater chance of error with the current tattooing technique. The isocenter marking device eliminates the need to draw lines on the patient's body using a marker. The alignment indicia included on the isocenter marking device guide the placement on the patient's skin when matched to the laser beams. This ensures accuracy of marking of up to about 100 percent of the time.

The isocenter marking device may minimize the chance of a needle stick to a user. Currently, a 19 gauge needle is used to stick the patient for each tattoo. The needle is held between two fingers and is exposed to the patient, the therapist tattooing, and any other persons who may potentially come into contact with the device. After giving a tattoo, the needle is then placed in a sharps container. With the isocenter marking device, the needle is hidden inside the device. Additionally, the needle is retractable. Once the tattoo has been given, the needle will retract back inside the plastic housing. The needle is not directly exposed to a user during the procedure. After the tattoo is given, it is discarded into a sharps container.

The isocenter marking device, according to the various embodiments, also avoids the need to tattoo a patient twice because the tattoo is not visible. Each therapist has their own technique when sticking the patient. Some therapists are afraid to hurt the patient when sticking them with the needle. Unfortunately, this leaves a tattoo that is not visible so the patient must be tattooed a second time. On the other hand, some are not afraid to stick the patient leaving a large tattoo. This is very uncomfortable for the patient because it means the needle was stuck too deep. The isocenter marking device includes a preloaded spring with the needle attached. When the button is pushed with the correct amount of pressure the spring is released forcing the needle into the patient's skin only 2 mm deep. This ensures the depth that the needle will penetrate the patient's skin every time. It will also consistently provide the same size tattoo. The need to tattoo a patient twice in the same spot will be eliminated.

Cleanup is easier with the isocenter marking device according to the various embodiments. With the current technique, the patient is left with an X drawn on their skin with a marker. There is also excess ink on their skin. The isocenter marking device, as described above according to the various embodiments, eliminates the need to mark the patient with a marker. The ink used for the tattoo is contained inside the device so only a small amount of ink is left on the patient, which is easily wiped off with an alcohol wipe.

The isocenter marking device, according to the various embodiments described above, may potentially meet all OSHA standards. The isocenter marking device includes its own supply of ink contained within the device. Once the ink pocket is punctured, the isocenter marking device cannot be reused. It is sterile, and has the exact amount of ink needed for one tattoo.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the above described features.

The following is claimed:

1. An isocenter marking device for marking an isocenter at a location on a patient's body, the device comprising:

a base having a periphery and a surface for placement on a patient including first and second alignment indicia, each alignment indicia in a plane generally parallel to the base surface, the first and second alignment indicia located within the periphery to define two linear paths extending to a region within the periphery of the base, wherein the first and second alignment indicia are configured for alignment with external alignment sources to facilitate alignment of the base over the isocenter;

an ink marker on the base, wherein the ink marker comprises at least one needle having a needle tip and is positioned relative to the alignment indicia on the base and within the periphery of the base for marking an ink mark on the isocenter on the patient's body; and an actuator on the base for actuating the ink marker and causing an ink mark indicating the isocenter to be made on the patient's body; and an ink well, wherein the at least one needle is driven through the ink well in response to actuation of the actuator.

2. The device according to claim 1, wherein the base further comprises an adhesive layer for securing the base to the patient's body.

3. The device according to claim 1, wherein the ink marker comprises at least one needle comprising a cavity adapted to retain and deliver a metered amount of an ink or dye into a patient's skin.

4. The device according to claim 1, wherein the actuator comprises a spring, wherein compression of the spring actuates the maker.

5. The device according to claim 1, wherein the alignment indicia comprises at least two orthogonal lines.

6. The device according to claim 1, wherein the actuator is disposed over the ink marker.

7. The device according to claim 1, wherein the base is self-sealing.

8. The device according to claim 1, wherein the base includes a conformal layer for conforming to a surface of the patient's body.

9. The device according to claim 1, wherein the base further comprises a spacer disposed between the ink marker and patient's body when the device is placed on the patient's body.

* * * * *